United States Patent [19]

Grahn et al.

[11] Patent Number: 5,553,500

[45] Date of Patent: Sep. 10, 1996

[54] TRIAXIAL NORMAL AND SHEAR FORCE SENSOR

[75] Inventors: Allen R. Grahn; Josephine M. Grahn, both of Salt Lake City, Utah

[73] Assignee: Bonneville Scientific Incorporated, Salt Lake City, Utah

[21] Appl. No.: 329,465

[22] Filed: Oct. 26, 1994

[51] Int. Cl.[6] .............................. G01L 1/25; G01N 29/26

[52] U.S. Cl. ...................... 73/628; 73/652; 73/862.043; 73/862.046; 73/862.637

[58] Field of Search ......................... 73/627, 628, 644, 73/652, 862.041, 862.042, 862.043, 862.046, 862.05, 862.541, 862.637, 597

[56] References Cited

U.S. PATENT DOCUMENTS

| | | | |
|---|---|---|---|
| 4,704,909 | 11/1987 | Grahn et al. | 73/DIG. 4 |
| 4,964,302 | 10/1990 | Grahn et al. | 73/628 |
| 4,998,441 | 3/1991 | Stuart | 73/862.046 |
| 5,209,126 | 5/1993 | Grahn | 73/862.046 |
| 5,295,399 | 3/1994 | Grant et al. | 73/862.043 |
| 5,341,687 | 8/1994 | Stan | 73/862.046 |

OTHER PUBLICATIONS

Bauer, F. Piezoelectric and Pyroelectric Polymers, *Polymers as Synthetic Metals Conference*, London, May 1983.

Begej, S., Fingertip–Shaped Tactile Sensor with Shear Force–Sensing Capability, NSF–88–50, *Abstracts of Phase I SBIR Awards, NSF*, 1988.

Cutkosky, M. R., et al., Skin Material for Robotic Fingers, *IEEE International Conference on Robotics and Automation*, Mar. 1987.

Grahn, A. R., et al., Six Component Robotic Force–Torque Sensor, *Final Report 178347*, 1987.

Grupen, R. A., et al. A Survey of General Purpose Manipulation, *International Journal of Robotics Research*, vol. 8. No. 1, Feb. 1989.

Hackwood, S., et al., A Torque–Sensitive Tactile Array for Robotics, *International Journal of Robotics Research*, vol. 2, No. 2, Summer 1983.

Harmon, L. D, Robotic Taction for Industrial Assembly, *Report No. 1. Dept. of Biomed. Eng. Case Western Reserve Univ.*, Oct. 1982.

Howe, R. D., et al. Review of Robotic Tactile Sensing, to be published, 1989.

Jacobsen, S. C., et al. Tactile Sensing System Design Issues in Machine Manipulation, *IEEE Robot Conf. Proc.*, 1987.

Nicholls, H. R., et al. A Survey of Robot Tactile Sensing Technology, *International Journal of Robotics Research*, vol. 8, No. 3, Jun. 1989.

Siegel, D. M., et al., A Capacitive Based Tactile Sensor, *SPIE vol. 579 Intelligent Robots and Computer Vision*, 1985.

Siegel, D. M., et al. Contact Sensors for Dexterous Robotic Hands, MS thesis, MIT, 1986.

Sinden, F. W., et al. A Planar Capacitive Force Sensor With Six Degrees of Freedom, *IEEE Robot Conf. Proc.*, 1986.

*Primary Examiner*—Hezron E. Williams
*Assistant Examiner*—Rose M. Finley
*Attorney, Agent, or Firm*—Trask, Britt & Rossa

[57] ABSTRACT

A triaxial force sensor using a hemispherical target embedded in a compliant layer such as an elastomer and having a plurality of ultrasonic transducers disposed in a plane at equal intervals about the target and vertically and laterally offset from the target. The transducers are oriented at an oblique angle to the plane, and aimed at the target in its rest position. The target is displaced by sufficient force applied to the surface of the compliant layer, which displacement alters the transit times of ultrasonic signals from the transducers which are reflected from the target. If at least three sensor units are employed non-colinearly, the six force-torque components, $F_x$, $F_y$, $F_z$, $M_x$, $M_y$, $M_z$, can be determined from the pulse transit times, the speed-of-sound in the compliant layer, the compressibility of the compliant layer, and the known geometry and spacing of the sensor units. Pairs of transducers may be rotationally offset from each other to determine different force-torque components. A plurality of sensors as described may be employed together in a multi-sensor array. An alternative embodiment employing both the amplitude and the transit time of an ultrasonic pulse is also disclosed.

31 Claims, 9 Drawing Sheets

TRIAXIAL NORMAL AND SHEAR FORCE SENSOR

BACKGROUND OF THE INVENTION

1. Field of the Invention

The present invention relates generally to force sensors, and more specifically to an ultrasonic sensor for the measurement of normal and shear forces.

2. State of the Art

With rare exception, tactile or contact-type sensors in the art respond to normal forces only. From the measurement of normal force distribution, three ($F_z$, $M_x$, $M_y$) of the six force-torque components ($F_x$, $F_y$, $F_z$, $M_x$, $M_y$, $M_z$) can be computed. These three components are the normal force and the two orthogonal torques in the plane of the sensor. Normal-force sensing is adequate for tasks involving object or feature identification, determining object location with respect to the sensor, and under some circumstances, estimating impending slip from the normal force and knowledge of the coefficient of friction between the object and the sensor surface.

However, for certain applications, such a limited sensing capability is inadequate. Examples of such applications include, without limitation, gasping and manipulation by a robot hand; measurement of forces generated by an object such as tire, shoe, boot or ski moving over the sensor; determination of pressure points, forces and movements of bodily extremities with respect to footwear such as athletic shoes, boots, and ski boots as well as sporting (golf clubs, tennis rackets, baseball bats) and industrial (hand tools, grips for electrically-powered tools) implements; determination of balance and gait analysis for athletic training and medical treatment and rehabilitation; use in a joystick, cursor control or other position-dependent control devices; and for accelerometers.

There have been several attempts to develop arrays of triaxial force sensors or full six-axis tactile sensors. For example, tactile array elements have been composed of magnetic dipoles embedded in an elastomer, the position and orientation of which were detected by magneto-resistive sensors. However, only one- or two-element sensors have been fabricated to prove feasibility of the concept. Another approach has employed sensors using emitters (charge or magnetic) embedded in a compliant layer. Emitter position is measured by an array of field-effect transistors or Hall-effect devices fabricated on a silicon substrate. Prototype sensors of this design were found to be highly sensitive to external fields.

A capacitance-based approach has also been attempted, but implemented only with respect to normal-force sensing. An existing, optically-based tactile sensor may have been modified to incorporate shear sensing capabilities. Presumably, the technique being investigated is the position monitoring of optical targets embedded in a substrate. However, such a design does not lend itself to incorporation into necessarily compact sensors as used in robot end-effectors, due, among other consideration, to the presence of a relatively large, stiff bundle of optical fibers exiting the sensor.

A miniature force-torque sensor has been developed by the assignee of the present invention. This sensor was intended for mounting on the gripping surfaces of robot end-effectors. The sensor consists of an elastomeric spring element joining two rigid parallel plates, one of which is mounted to the end-effector. Ultrasonic pulse-echo ranging through the elastomer is used to detect fine movements of one plate relative to the other. The sensor is compliant, the degree thereof as well as the sensitivity and load range of the sensor being alterable by changing the elastomer composition. The six force-torque components may be calculated from the transit times and specifically times-of-flight (TOF) of a plurality of differently-aimed pulse-echo signals as one plate is deflected with respect to the other under application of force. A further description of the aforementioned sensor appears in U.S. Pat. No. 4,704,909, assigned to the assignee of the present invention, and incorporated herein by reference.

Other force sensors developed by the assignee of the present invention, which sensors employ pulse-echo ranging, are U.S. Pat. Nos. 4,964,302 and 5,209,126, assigned to the assignee of the present invention and incorporated herein by reference. The sensors disclosed in these two patents do not, however, have triaxial force component determination capability.

SUMMARY OF THE INVENTION

The sensor of the present invention provides a highly accurate, robust and relatively inexpensive sensor, in comparison to prior art sensors known to the inventors. In its preferred embodiments, the sensor employs transit time of reflected ultrasonic pulses to determine three force components. The sensor may be used singly, or in arrays incorporating a plurality of basic sensor units.

A preferred embodiment of the basic sensor unit of the present invention comprises a target suspended above laterally- and vertically-offset ultrasonic transducers, each having an emitting and receiving capability. The target is preferably of spherical or hemispherical shape; if the latter, the flat portion of the hemisphere is oriented parallel to the plane in which the transducers are located, with the arcuate portion of the hemisphere facing the plane. The transducers are aimed at the target and thus emit signals at an oblique angle to the transducer plane. The target is preferably embedded in a compliant material, such as an elastomer layer, which extends at least partially between the target and the transducers. Forces applied to the surface of the elastomer layer above the target distort the elastomer and may move the target both vertically and horizontally with respect to its original position. Target position is measured by ultrasonic echo-ranging; that is, one measures transit time of the obliquely-oriented ultrasonic pulses which pass from each transducer through the elastomer, impinge upon the target and reflect back to that transducer. From the transit time measurement and knowledge of the speed-of-sound within the elastomer, the distance from the transducer to the target can be calculated. Since a plurality of transducers are disposed about and aimed at the target, target movement results in a plurality of different transit times, from which force components can be calculated using the known compressibility characteristics of the compliant layer. At least three, and preferably four, transducers are aimed at each target for triaxial force determination.

The basic sensor unit may also be employed in a joystick or cursor control device, or as an accelerometer. In the latter case, a second group of transducers may be placed over the target in contraposition to the first set, if desired, for the contemplated application.

If desired, a plurality of basic sensor units may be arranged in a planar sensor array, the term "planar" being used herein to denote not only a sheet-like array extending in a linear plane, but also such an array which is concave, convex, or otherwise arcuate or non-linear in configuration, as required by the particular application.

Sensor accuracy may be enhanced with minimum time skew by pulsing each transducer in rapid succession before the echo of the preceding pulse has returned to the transducer. The time lag or difference of the second and successive pulses in a pulse burst after the first pulse is subtracted from the transit time of that pulse. The resulting, lag-compensated transit times of the pulses in a burst are then averaged.

If an array is formed, the scan rate to effect continuous scanning of all targets in the sensor array may be enhanced by rapidly pulsing transducer columns in succession before the pulses from the previously-pulsed columns have reflected and returned to the transducers of those columns.

An alternative transit time measurement technique, in lieu of pulsing an ultrasonic signal toward the target, is to generate a continuous oscillatory signal or several cycles of continuous signal and to measure the phase shift between the outgoing and returning (reflected) signal. Hence, the term "transit time measurement" as used herein is intended to encompass such measurement by phase shift determination.

DETAILED DESCRIPTION OF THE PREFERRED EMBODIMENTS

The force measuring technique for the sensor of the present invention is, in its simplest form, based upon ultrasonic pulse-echo ranging between a movable target and a transducer, although, as noted above, phase-shift measurement of an oscillatory signal may also be employed to determine signal transit time. The target is embedded in a deformable medium having known sound-transmission attributes, the medium extending between the target and the transducer. It is currently preferred that this deformable medium comprise an elastomer, and for purposes of convenience, the term "elastomer" will be employed in this discussion, although it will be understood that other materials, such as gels, robber compounds, plastics, liquid-filled bags or balloons, etc., may be employed. Alternatively, a spring or springs such as coil, leaf, belleville or other spring configuration supporting a target may be employed in combination with a sound-transmitting medium to convey the ultrasonic signals. The target moves when the supporting medium is distorted or compressed by sufficient force. The distance between the target and the transducer is determined from the time it takes an ultrasonic signal to traverse the intervening medium and return. From this time interval measurement, hereinafter "transit time", knowledge of the speed-of-sound in the medium and the medium's modulus (i.e., the stress required to produce a particular degree of compression), the forces compressing the medium can be calculated.

Two basic principles are involved in pulse-echo distance measurement. First, the speed-of-sound, c, in the medium (elastomer) is known so that its thickness between the target and the transducer can be determined from the two-way transit time, t, of the pulse, by:

$$d = \tfrac{1}{2} c t \tag{1}$$

The second principle is that the interface between the target and the elastomer must reflect the pulse. Therefore, it is imperative that the target have an acoustic impedance which differs significantly from that of the elastomer.

The time required for an ultrasonic pulse to make a round trip between the transducer and the target is given by equation (1) above. For 3 mm of silicon rubber, the time of flight (transit time) of the pulse is about 6 microseconds. Therefore, if the expected maximum force compresses the rubber to 60% of its original thickness (1.2 mm compression) and it is required to resolve this force to one part in 200

(corresponding to a distance resolution of 6 microns), then the ultrasonic pulse transit time must be resolved to within 12 ns.

Polyvinylidene Fluoride (PVDF) is preferably used for the transducer materials in the sensor of the invention. The material has a low mechanical Q, low acoustic cross coupling between adjacent array elements, and simplifies array fabrication. PVDF is a thin-film polymer material which is demonstrated to be five to ten times more piezoelectric than crystalline quartz when stretched and poled. Other polymers which offer a piezoelectric capability may also be employed. It should be understood, however, that still other transducer materials, such as ceramics, may be used in appropriate circumstances such as in high-temperature environments.

A great degree of freedom is available in the choice of an appropriate elastomer for target support and signal transmission. The primary function of the elastomer is to act as a linear spring. Stated another way, the elastomer compresses in direct proportion to the amount of force applied. Ideally, the elastomer's force versus compression characteristics should be linear so that a simple proportionality constant can be used for force or pressure calculations.

The use of an elastomer-embedded target provides a number of benefits. For example, the exposed surface of the elastomer layer containing the target can sustain limited wear and damage without degradation of sensor performance. In addition, the elastomer layer above the reflectors may be made so that it can be replaced when it becomes damaged or contaminated. The exposed surface can be easily textured to aid in grasping or to reduce the normally high coefficient of friction (if rubber is used) to prevent sticking. Finally, sludge, mud or other contaminants on the sensor pad surface, or the manipulation of rubber objects, would not affect sensor performance.

Figure 1A:
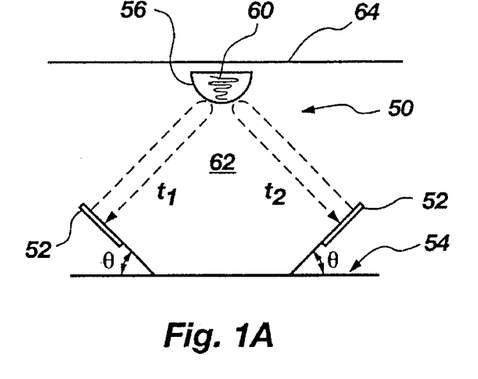
FIGS. 1A and 1B are schematic side elevations of an illustrative transducer and target arrangement for two-dimensional monitoring of target position.
Figure 1B:
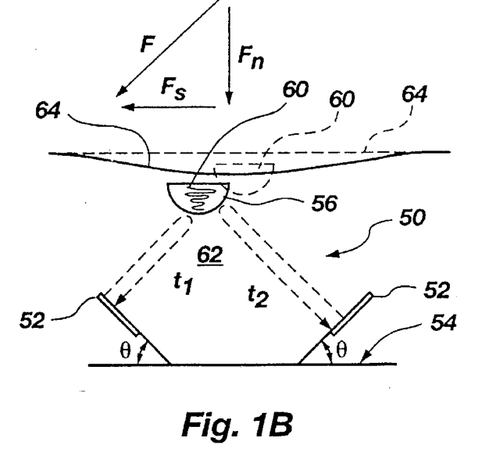

FIGS. 1A and 1B depict a simplified transducer and target arrangement 50 according to the present invention for determining target position in two dimensions. Ultrasonic transducers 52, located in a common plane 54, are aimed at the arcuate surface 56 of hemispherical target 60. Transducers 52 are both vertically and laterally offset from target 60, so that ultrasonic pulses travel to and from target 60 through medium 62, typically an elastomer, at an oblique angle. With this configuration, the normal force and one of two shear-force components can be measured. The sum of the transit times from the transducers, $t_1+t_2$, is proportional to the normal force component, $F_z$. The difference in transit times, $t_2-t_1$, is proportional to the shear force component, $F_x$ or $F_y$.

The proportionality constants inferred above depend upon the speed-of-sound in the compliant, acoustically transparent medium 62 located between the transducers 52 and the target 60 (in order to convert the time interval measurement into distance), the appropriate elastomer stiffness constant, the geometry describing the positions of the transducers and target, and target geometry.

Figure 2:
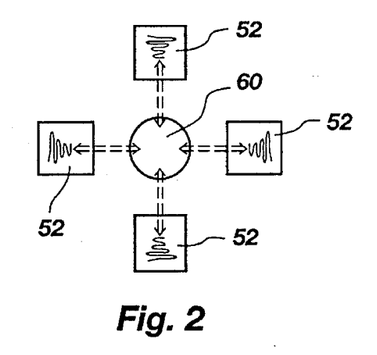
FIG. 2 is a schematic top elevation of a target and four-transducer configuration as may be employed in a basic sensor unit.
Figure 3:
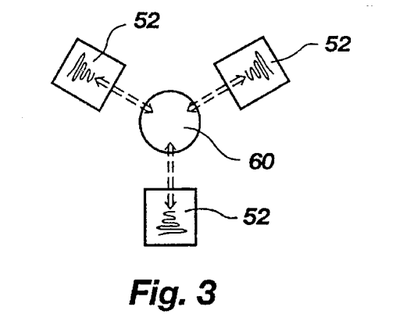
FIG. 3 is a schematic top elevation of a target and three-transducer configuration as may be employed in a basic sensor unit.

As shown in FIG. 1, when no force or pressure is applied to the contact surface 64 of the compliant medium (elastomer) in which the target is embedded, the transit times $t_1$ and $t_2$ are equal. When a force F is applied to contact surface 64, the medium 62 distorts and compresses in the direction of the force vector, and target 60 is displaced in proportion to the level of force F applied. Transit times $t_1$ and $t_2$ then differ, and from this difference the target location may be calculated. For measuring a second shear force component, another pair of transducers 52, as shown in FIG. 2, may be positioned at right angles to the first pair. If desired, only three transducers 52, as shown in FIG. 3, may be disposed about a target 60 at 120° intervals for measurement of the three force components. Such an arrangement minimizes the number of transducers required, but may not be desirable, as it complicates the otherwise straightforward mathematics involved in calculating the target position, and it is difficult to fabricate multi-sensor arrays using this arrangement.

The angled ultrasonic pulses (i.e., angle Θ in FIGS. 1A and 1B) can be obtained by mounting the transducer material on angled facets, mounting the transducer material on a flat surface and using reflectors to reflect the pulses at the desired angle, or mounting the transducer material on a flat surface and using wedges of a suitable material like prisms to refract the pulses at the desired angle. The first alternative is preferred, due to the bulk added to the sensor by the other two alternatives, and, in the third alternative, the severe constraints placed on the acoustic properties of the refracting wedge material. For arrays with a large number of basic sensor units, the PVDF transducer material for a large number of transducers should be installed as a single sheet in a single operation rather than employing single, discrete transducer elements or strips of such elements. This approach renders multi-sensor arrays much more economical, as well as ensuring more accurate transducer placement.

Figure 4:
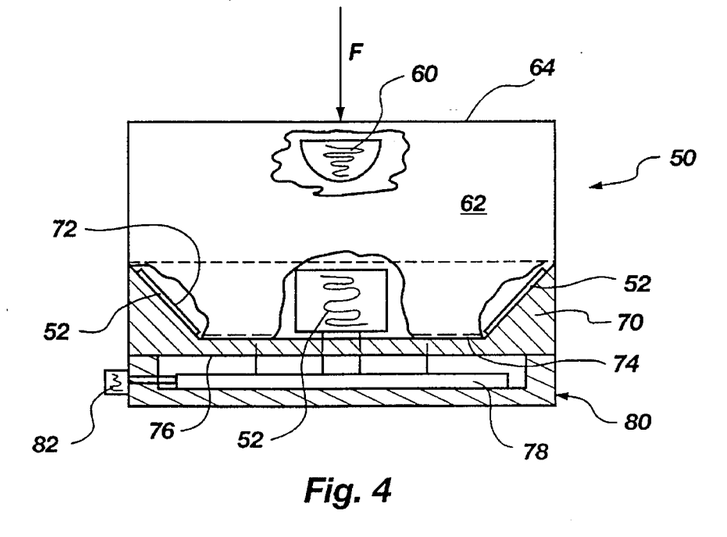
FIG. 4 is a partial section side elevation of a preferred configuration for a four-transducer basic sensor unit.
Figure 12:
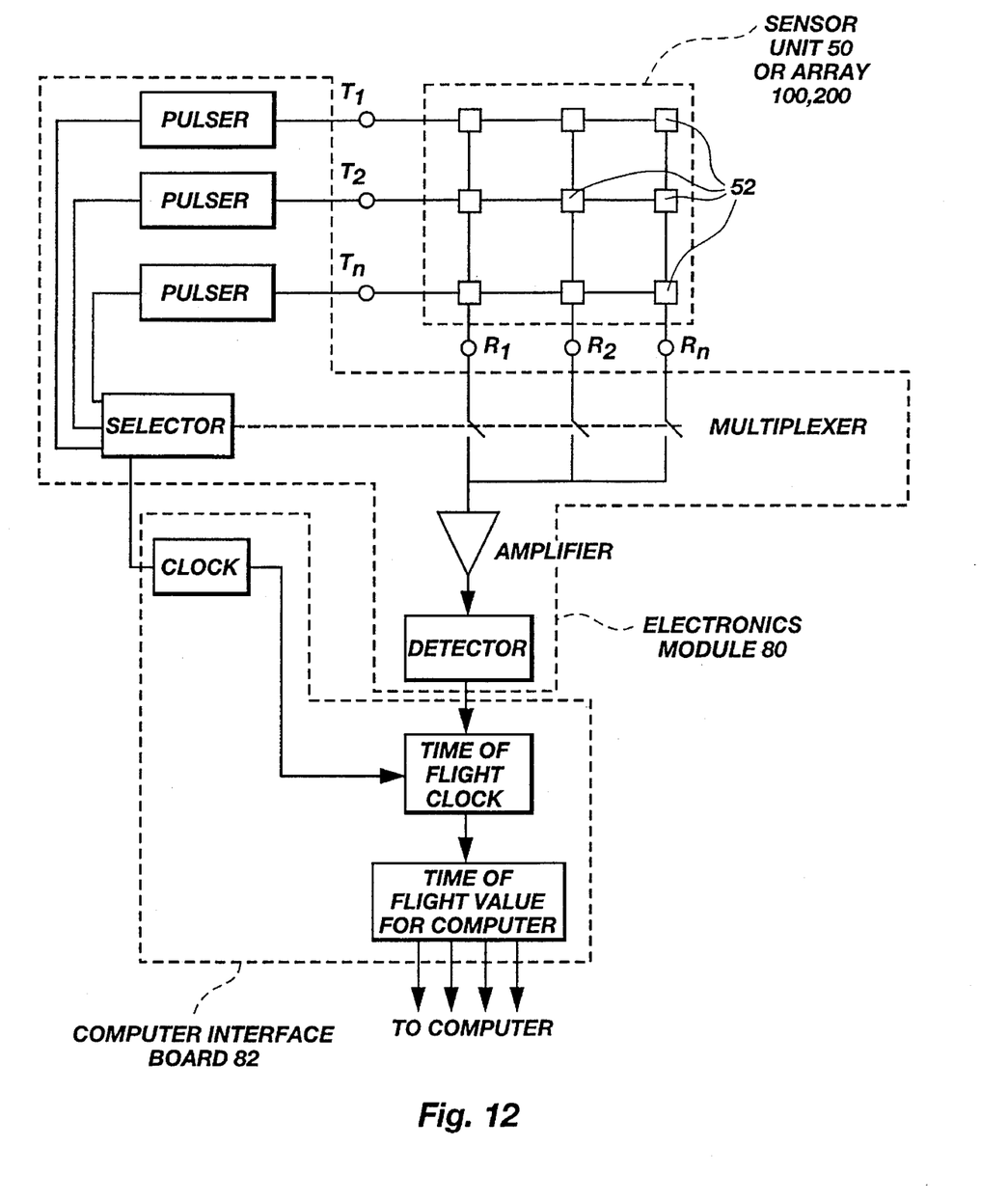
FIG. 12 is a schematic of the processing circuitry employed to convert pulse transit times from transducers aimed at a target into the actual target position.

FIG. 4 depicts a preferred physical configuration for a four-transducer basic sensor unit 50 in accordance with the present invention. The four PVDF film transducers are mounted to a substrate 70 with an inner wall 72 set at a 45° angle. Target 60 is embedded in a compliant medium 62 which extends between the target 60 and the transducers, filling the void therebetween. The upper surface 64 of medium 62 provides a contact surface for application of a force, F. Wires or printed conductors, shown in broken lines at 74 (preferably the latter, and molded into or onto substrate 70 at the time of its fabrication) extend through substrate 70 to the lower surface 76 thereof, where they communicate with conductors of the electronics 78 of electronics module 80 disposed underneath substrate 70. Electronics module 80 then communicates with a host processing unit such as a personal computer (PC) via connector 82 and a suitable interface board. FIG. 12 depicts a schematic of the circuitry of the electronics module 80 and interface board with a sensor unit of array 100, wherein the transducers 52 are selected and pulsed, the ultrasonic echo signals are amplified and detected, and the corresponding transit times are measured. The detected pulse transit times are converted to force component values by the PC using the known speed-of-sound and compliancy characteristics of the medium supporting the target 60.

FIGS. 5, 5A–5D and 6 depict a preferred embodiment of a single-level, multi-sensor array 100 of the present invention. For the sake of clarity, reference numerals previously employed are used again to identify the same elements. In array 100, a plurality of hemispherical targets 60 (nine in this instance, for exemplary purposes only, and not by way of limitation) are disposed above transducers 52, each target 60 having four transducers 52 aimed at it, preferably from a common distance and angle. If a wide angle (e.g., 25° to the sensor plane) is employed, the sensor unit may be made thinner, but shear force sensing capability is somewhat diminished. If a closer angle is employed (e.g., 60° to the sensor plane), greater shear force sensitivity results. Targets 60 are embedded in a compliant medium 62, which provides a contact surface 64 for the application of a force, F. A first plurality of rows of transducers 52 are carried by perforated substrate 102, and a second plurality of rows of transducers 52 running at a 90° angle to the first plurality are carded by ridged substrate 104.

As can be seen by viewing FIGS. 5, 5A, 5C and 5D together, segments 106 of perforated substrate 102 are received in valleys 108 of ridged substrate 104. When the two substrates are assembled, windows 110, the widest portions of which lie along ridgelines 112, provide transducers 52 of ridged substrate 104 with a clear field of fire at targets 60. Compliant layer 62, with targets 60 molded therein, includes protrusions 66 which are received in each recess flanked by four transducers 52 when perforated and ridged substrates 102 and 104, respectively, are assembled.

Figure 5:
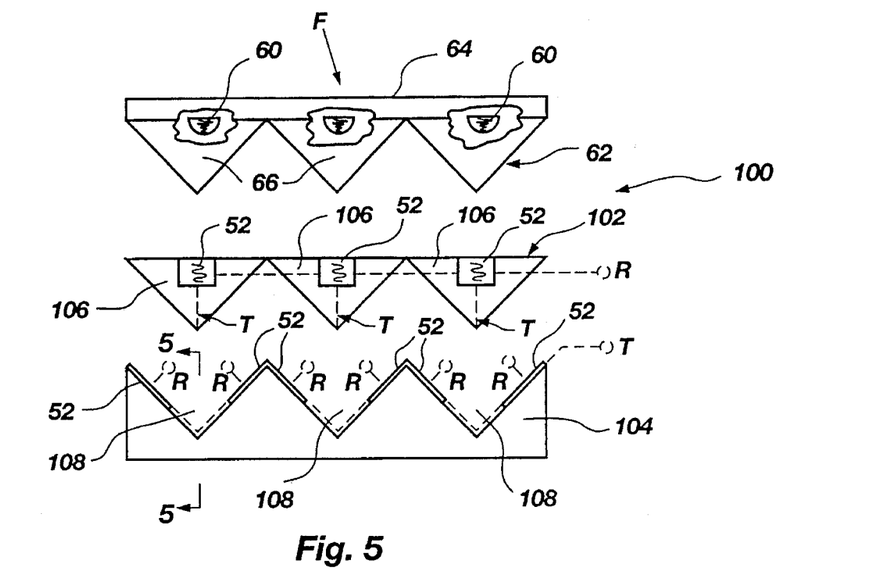
FIG. 5 is a schematic exploded side elevation of a preferred configuration for a single-level, multi-sensor array.
Figure 5A:
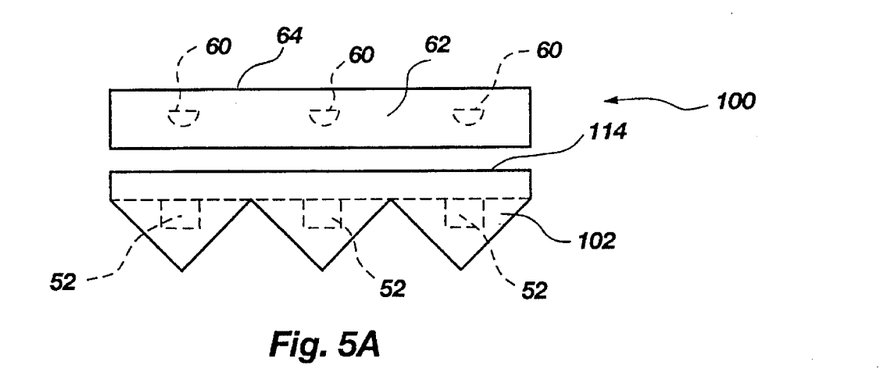
FIG. 5A is a depiction of an alterative layering arrangement for target placement and transducer protection.
Figure 5B:
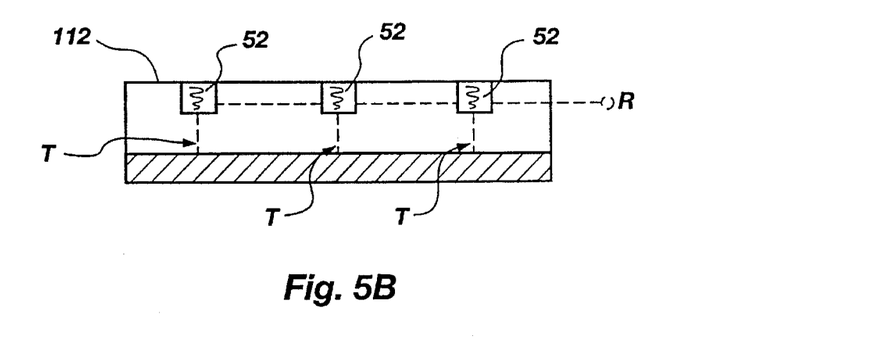
FIG. 5B is a section taken along lines 5—5 in FIG. 5.
Figure 5C:
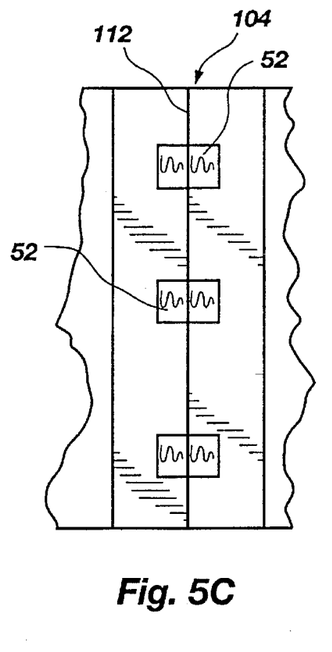
FIG. 5C is a top elevation of a ridgeline of the lower substrate of the array.
Figure 5D:
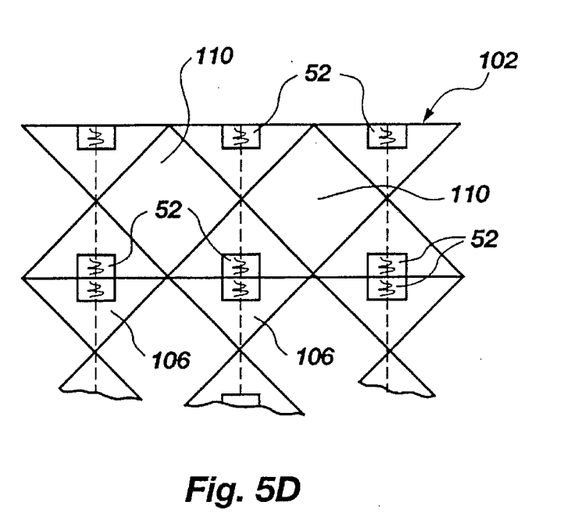
FIG. 5D is a top elevation of a portion of the segmented upper substrate of the array.

As shown in FIG. 5A, targets 60 may be embedded in a separate compliant layer 62, which is easily removable and replaceable for repair purposes and to provide a ready means for altering the compliancy of the support for targets 60 to accommodate differing anticipated force ranges. In this case, substrate 102 is molded so as to have transducer 52 embedded therein as shown and to provide a continuous, planar upper support surface 114 for compliant layer 62. This arrangement also offers better protection for the transducers than the arrangement of FIG. 5.

Figure 6:
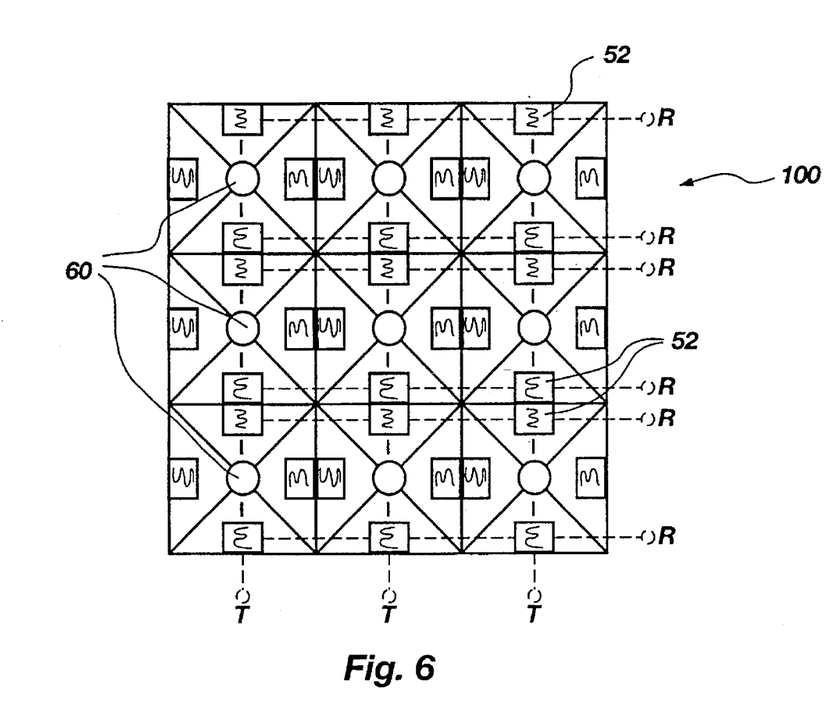
FIG. 6 is a schematic top elevation of the single-level, multi-sensor array of FIG. 5.

As shown in FIGS. 5 and 6, transducers 52 are activated in columns by transmitting conductors T to emit ultrasonic pulses which are then reflected from targets 60 and received by the same transducers 52 from which they are emitted, the received signals being output from transducers 52 via receiving conductors R. This arrangement is depicted and described in more detail with respect to FIG. 8.

It will be readily understood that the medium extending between targets 60 and transducers 52 must be sufficiently acoustically transparent and nonrefractive for the ultrasonic pulses to travel therethrough without excessive attenuation and via a direct and consistent path. The term "medium" of course, is not limited to single-component mediums, but may comprise multiple layers. Unless the ultrasound signals contact the interface of two medium components at about 90°, it is desirable that the components' indices of refraction be substantially similar.

Figure 7A:
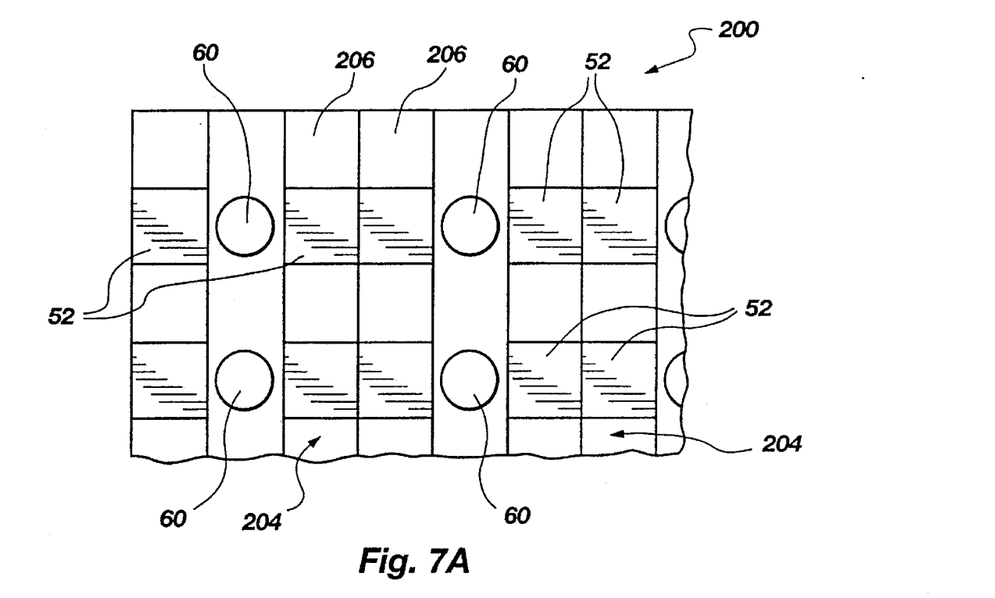
FIG. 7A is a schematic top elevation of an upper transducer level of an alternative multi-level, multi-sensor array embodiment of the invention.
Figure 7B:
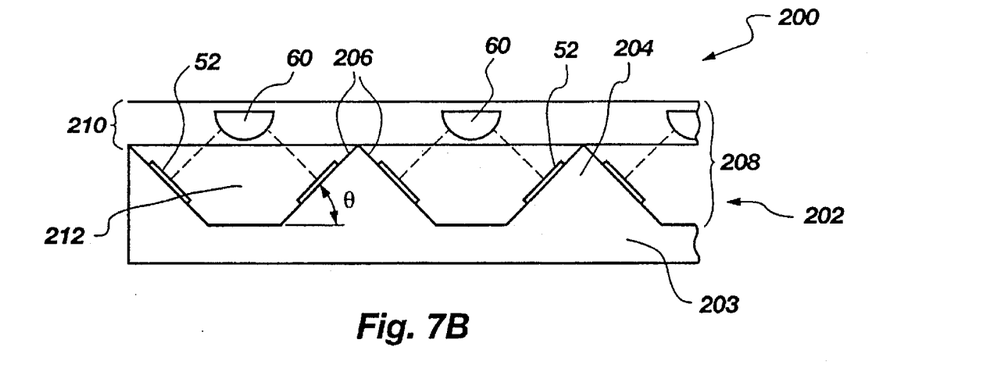
FIG. 7B is a schematic side elevation of the upper transducer level depicted in FIG. 7A.

An alternative multi-level, multi-sensor array embodiment 200 of the invention is depicted in FIGS. 7A through 7D. Upper transducer level 202 includes an acoustically-transparent substrate 203 having a plurality of ridges 204 which, in three dimensions, would extend outwardly from the plane of the drawing, the ridges each having two sides 206 disposed at the same angle $\Theta$. PVDF transducers 52 are located at predetermined intervals along the ridges, as shown in FIG. 7A. Each of a plurality of targets 60 is located between a pair of transducers 52 aimed at that target. As shown in FIG. 7B, the targets are located "above" the transducers 52 in upper level 202, the term "above" being relevant only insofar as the drawing is concerned, it being understood that the sensors and sensor arrays of the present invention may be used in any orientation.

In one arrangement, the ridges 204 may project into the compliant, acoustically-transparent, nonrefractive elastomer layer 208 in which the targets 60 are embedded. It may be preferred for some applications to fully embed the ridges 204 and transducers 52 in one layer of elastomer or, alternatively, in a substantially non-compressible but acoustically transparent material layer 210, such as high durometer urethane compound to better protect the transducers, and to locate the targets in a separate compliant layer 212 thereabove. This also permits easy replacement of the targets and compliant upper layer 212 in the event of damage while the transducers remain unaffected.

Figure 7C:
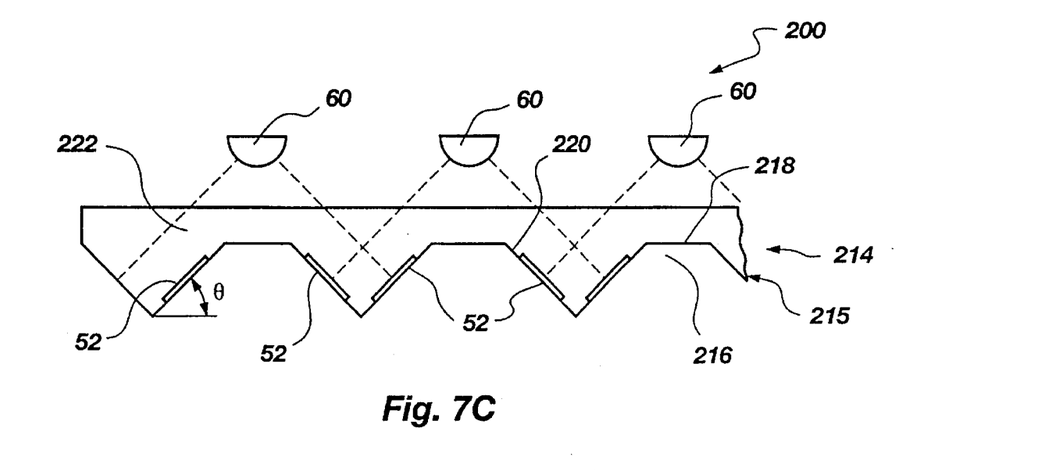
FIG. 7C is a schematic side elevation (rotated 90° about the vertical with respect to FIG. 7B) of a lower transducer level, of the multi-level multi-sensor array.

FIG. 7C depicts the lower level 214 of multi-sensor array 200. Lower level 214 is similar to upper level 202 and includes an acoustically-transparent substrate 215 including ridges 216, but ridges 216 in lower level 214 are truncated at their tops, providing flat upper surfaces 218 flanked by angled side surfaces 220 on which transducers 52 are mounted. Truncation of the ridges reduces the depth of the assembled sensor array 200, which is desirable for most applications. The transducers of lower level 214 transmit their pulses through the acoustically transparent material 222 overlying the lower level transducers 52, then through the upper substrate 203 and one or more higher layers such as 208, 210 and 212, depending upon the design employed, to reach targets 60 and reflect therefrom back to the lower level transducers.

Figure 7D:
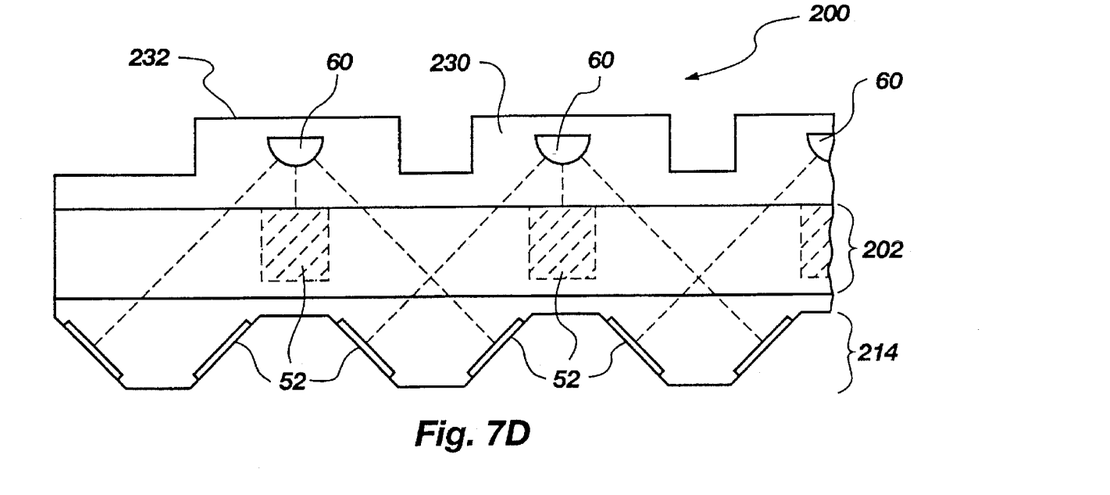
FIG. 7D is a schematic of the assembled multi-level, multi-sensor array.
Figure 11:
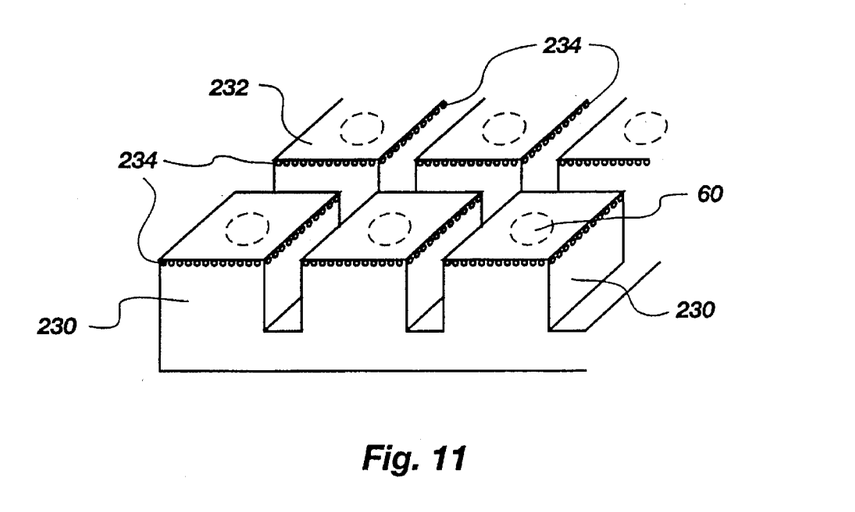
FIG. 11 is a perspective view of a plurality of basic sensor units incorporated in a multi-sensor array which includes a reinforced contact layer to accommodate high forces without degradation.

As shown in FIG. 7D, when assembled, sensor array 200 includes upper level 202 and lower level 214 at right or 90° angles, relative to the vertical. This rotational offset of the upper and lower levels 202 and 214 permits, as shown, the pulses from the transducers 52 of both upper and lower levels 202 and 214 to reach the targets 60 without interference. It is also noteworthy, again with reference to FIG. 7D, that the transducers 52 of lower level 214 are aimed at targets 60 which are farther laterally distant, permitting equal angles for transducer orientation in both levels. Finally, also as shown in FIG. 7D, it may be desirable to segment the upper elastomer layer containing the targets 60 into discrete blocks 230, each block being free to move relatively independently of the others. Such a configuration can reduce hysteresis and help prevent the embedded targets 60 from separating from the elastomer. Also, in some high-force applications, it may be desirable to reinforce the exposed elastomer pad surface 232 (see FIG. 11) with, for example, steel, Kevlar, nylon or other cord material 234 such as is employed in vehicle tires, or even a metal plate or non-woven mesh. It may also be desirable to coat or cover the pad surface 232 with a more wear-resistant material or one having a different coefficient of friction with respect to that of the element contemplated to apply force F to it, so as to enhance or reduce friction between the pad surface 232 and the contacting element.

With respect to the multi-layer embodiment 200, it again is important to emphasize that the material between the lower level of transducers 52 and the target 60 must be both sufficiently acoustically transparent and nonrefractive so as to avoid undue signal attenuation. In other words, the reflection coefficient for the interfaces between material 222 and substrate 203 and between the material 210 and the elastomer layer 212 should be close to zero. Stated another way, the acoustic impedance of the materials on either side of these interfaces should be approximately equal. Therefore, the product of material density times speed-of-sound needs to be about the same for both materials.

Urethane materials appear to be most promising for fulfillment of these requirements. Urethanes are tough, abrasion resistant and have high tear strength. They are also easy to bond to and readily pass ultrasonic waves. Furthermore, urethane compounds are available which can be formulated to have a wide range of harnesses, from approximately 15 Shore A to 75 Shore D durometer. In many applications, the first would be more than soft enough for the sensor pad or elastomer layer in which the targets 60 are embedded. The latter would be almost rigid and thus entirely strong enough for the substrate material and protective layers overlying the transducers mounted on the substrates. Since all compounds are urethanes, their product of density and speed-of-sound can be made relatively close. Of course, it is contemplated that other materials such as natural rubbers, silicone rubbers, neoprene, butyl rubbers, etc., may have equal utility for certain applications. Since the speed-of-sound through silicone rubbers is about ⅓ less than through urethanes, better resolution may be obtained via use of the former. In addition, softer silicone compounds than urethanes are currently available, making silicones more desirable for some applications.

It should also be noted that ultrasonic pulses from lower level transducers may pass through the PVDF layers of the upper level, as well as through the substrate material itself. This presents little difficulty, as the PVDF material is almost acoustically transparent for this application; its acoustic impedance is close to that of urethane. Furthermore, it is very thin, relative to the acoustic wavelength employed, and the metallization on the PVDF has little effect on attenuation since it is very thin.

Figure 8:
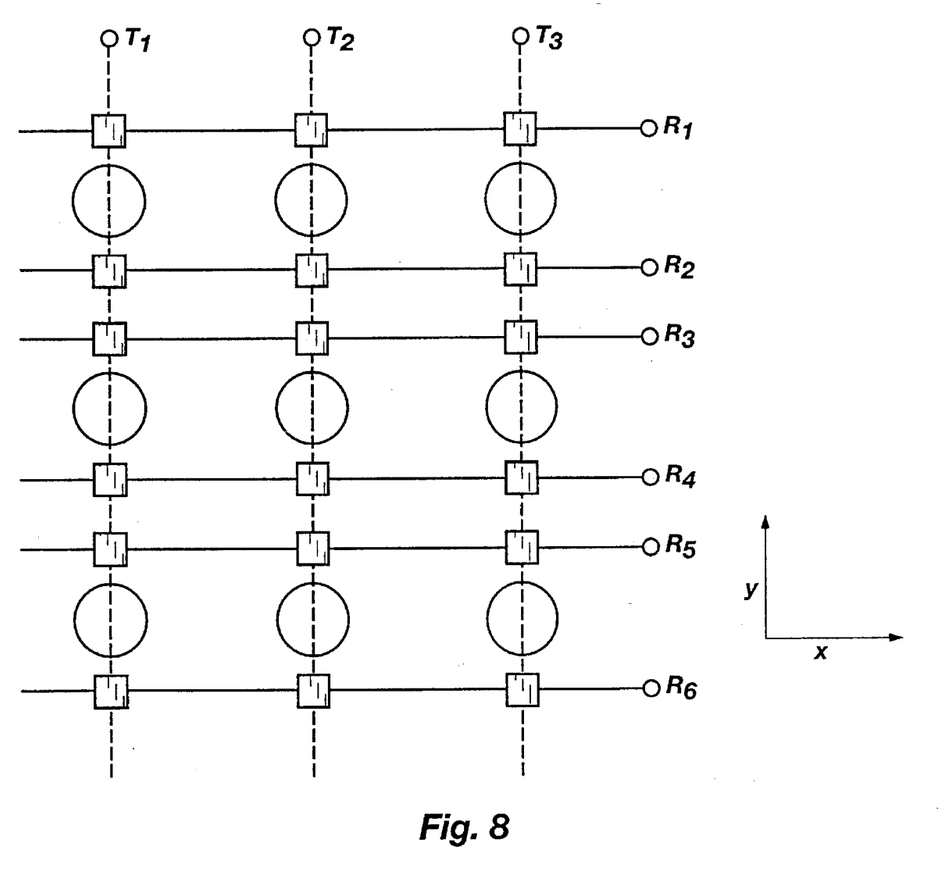
FIG. 8 is a wiring schematic of an array of transducers which may be employed with either the preferred or alternative embodiments of the multi-sensor array of the present invention.

FIG. 8 schematically depicts, from above, a wiring circuit which may be employed in either a single or multi-level, multi-sensor array for measuring the normal force $F_z$ and the $F_y$ shear force component. To prevent time skew in the $F_y$ measurement, one transmitting column such as $T_1$ would be pulsed and echoes would be received on the two receiving rows associated with the same site, such as $R_1$ and $R_2$, or $R_3$ and $R_4$, or $R_5$ and $R_6$. That is, there would be two parallel receiving/detecting channels associated with each target 60 associated with transmitting column $T_1$. Another, similar array structure contains the PVDF transducers and conductors for measuring $F_x$, the other structure being, as previously noted, rotated 90° with respect to the first.

Figure 9:
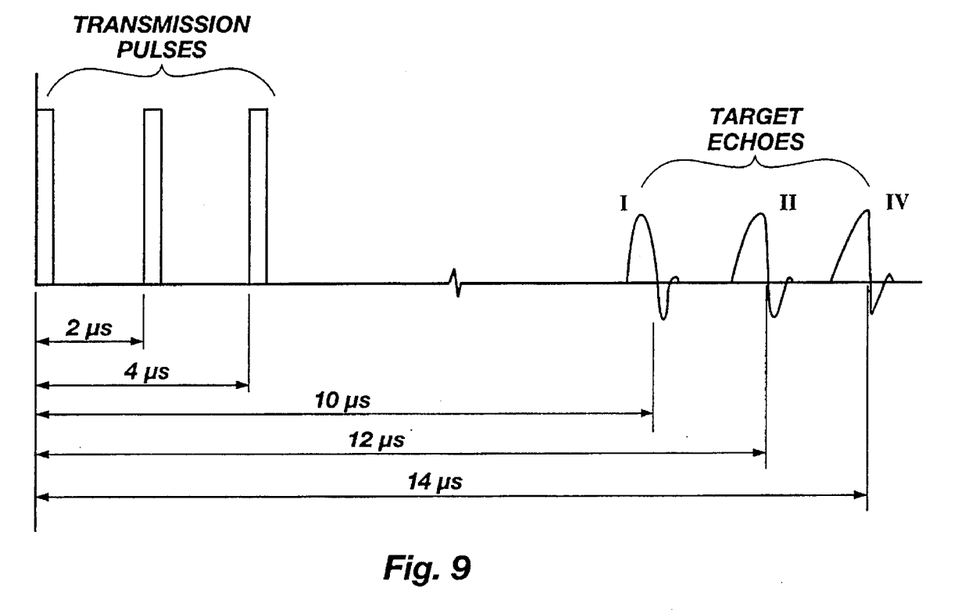
FIG. 9 is a timing schematic illustrating a technique of pulsing a transducer or column in a burst of closely time-spaced pulses to obtain an average value with minimum time skew.

FIG. 9 is an exemplary timing schematic for a technique permitting averaging of TOF measurements from and back to a single transducer 52 (at the intersection of one column and one row, as shown in FIG. 8), with minimal time skew. In the drawing figure, three excitation pulses are applied to the same transmitting column in rapid succession. The three echoes, I, II and II, produced by reflection of these pulses from a target 60 are detected in rapid succession. The pulses are emitted at 2 µs intervals, as shown. When echo II is detected, 2 µs is subtracted from its overall TOF value of 12 µs (12 µs–2 µs=10 µs). Similarly, 4 µs is subtracted from the overall TOF for echo III. The resulting TOF values for all three echoes are then averaged. Using such a "rapid-fire" pulsing technique, it takes only 14 µs, and not 30 µs, to make the three measurements. The above timing intervals and TOF figures are not meant to be accurate, but merely illustrative of the technique.

Figure 10:
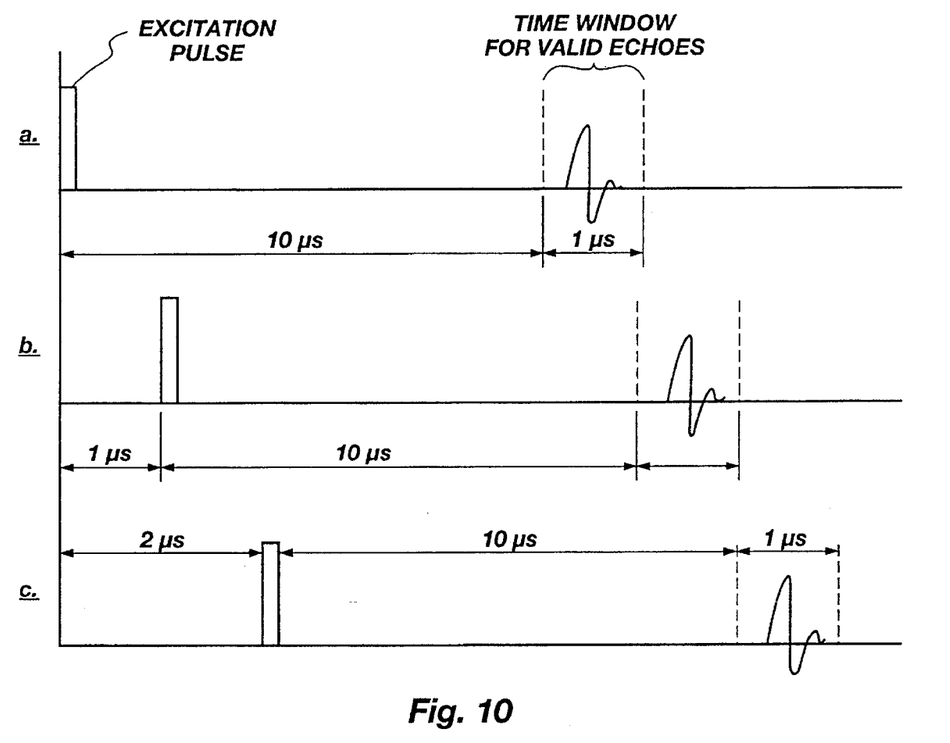
FIG. 10 is a timing schematic illustrating a technique of pulsing transducer columns in a multi-sensor array in rapid succession to effect continuous scanning of target positions.

FIG. 10 is an exemplary timing schematic for a technique of pulsing transmitting columns T (see FIG. 8) in rapid succession to increase the scan rate of the sensor array. Column a is pulsed, then b, then c, at 1 µs intervals. As shown, it would take only 13 µs to receive three echoes. The alternative of pulsing a column and waiting until the echo is detected before pulsing another column would take 11 µs per measurement, or 33 µs for detecting three echoes. Again, the stated timing intervals and TOF figures are not meant to be accurate, but merely illustrative of the technique.

To complete the sensor system according to the present invention, a few additional processing circuitry components are required. Specifically, an electronics module is employed to select and excite the array elements and multiplex the high-gain receiving amplifier. The module may be located at the sensor site or remotely therefrom. The module is also connected to a custom interface board in an IBM-compatible personal computer or other host processing unit. FIG. 12 is a schematic of the processing circuitry with the electronics module connected to a basic sensor unit or multi-sensor array, and to the interface board in the host processing unit.

Figure 13:
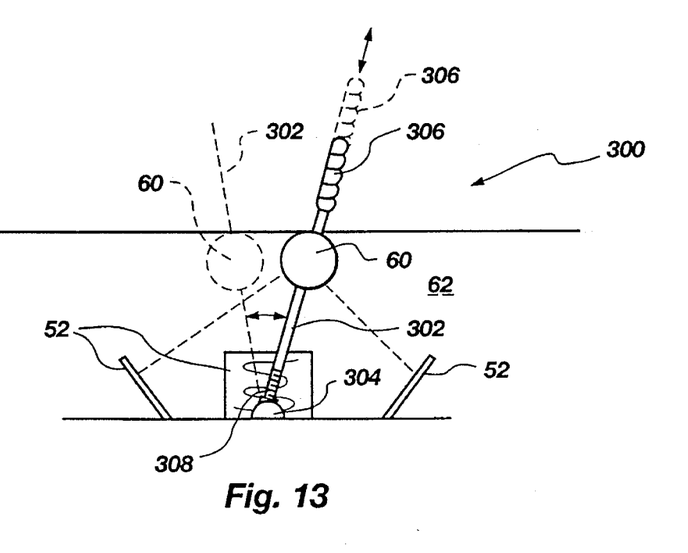
FIG. 13 is a schematic side elevation of the sensor unit of the present invention employed in a joystick.

FIG. 13 depicts a basic sensor unit 50 modified into a position-dependent control device 300 having four transducers 52 which has been modified by suspending target 60 from a joystick shaft 302 which is mounted to a universal or other flexible joint 304, providing the ability for a user to grasp a handle 306 at the upper end of the joystick shaft 302 and move it in any direction, including axially as shown in FIG. 13, due to the presence of spring element 308. Thus, the position of the joystick shaft 302 may easily be related to the transit times of the ultrasonic signals emanating from the transducers 52 through a sound-transmitting medium 62 interposed between target 60 and the transducers. This modification of the invention has ready applicability in joysticks for vehicle control, including aircraft, and for computer applications including cursor control and video games, as well as for commercial and industrial applications wherein the position of a control or sensing member is desired to be ascertained. Of course, the joystick shaft 302 may also be spring-biased to return to a central or other desired rest position when no force is applied.

Figure 14A:
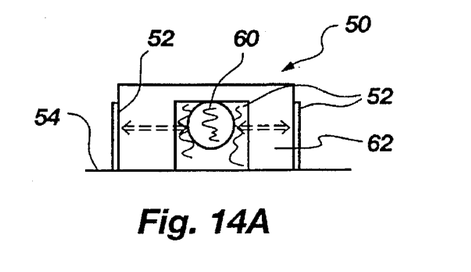
FIGS. 14A and 14B are schematics of the sensor unit of the present invention specifically adapted for use as an accelerometer.

FIG. 14A depicts the basic sensor unit 50 modified by positioning of the transducers 52 in a vertical orientation, with target 60 in the middle of the transducer group. Such an arrangement may be readily used as an accelerometer for forces in the plane 54 of the transducers 52, as movement and time of movement of target 60 in the surrounding compliant medium 62 responsive to acceleration or deceleration is easily measured. Such a modification of the invention may easily be used in a motor vehicle as a trigger for the deployment of airbags, particularly due to the recent development and emphasis on side-impact airbags by several manufacturers. Of course, if only fore-and-aft acceleration and deceleration are desired to be measured a sensor unit employing only two transducers would suffice.

Figure 14B:
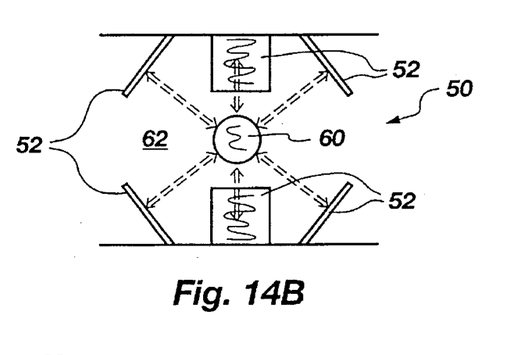

FIG. 14B depicts the basic sensor unit 50 augmented by the addition of four more transducers 52, arranged as the original four, but disposed above target 60. This modification of the invention is particularly suited for use as a triaxial accelerometer, such as are employed in aircraft and missile guidance systems, in test equipment for crash and other tests where acceleration and deceleration data is desired, and to control adjustable vehicle suspensions. Movement and time of movement of target 60 suspended within compliant medium 62 in any direction responsive to acceleration and deceleration forces is easily and accurately ascertained.

Figure 15:
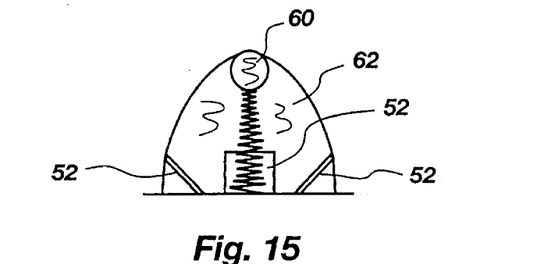
FIG. 15 is a schematic of a spring-supported target version of the invention.

FIG. 15 shows an embodiment of the sensor of the invention wherein target 60 is suspended on a spring 308 such as a coil spring, and a sound-transmitting liquid or gel medium 62 is interposed between transducers 52 and target 60. Of course, other spring types, such as belleville or leaf, might be employed, and it is contemplated that a plurality of springs might be used to support target 60 from below, from the side, and from above.

Figure 16:
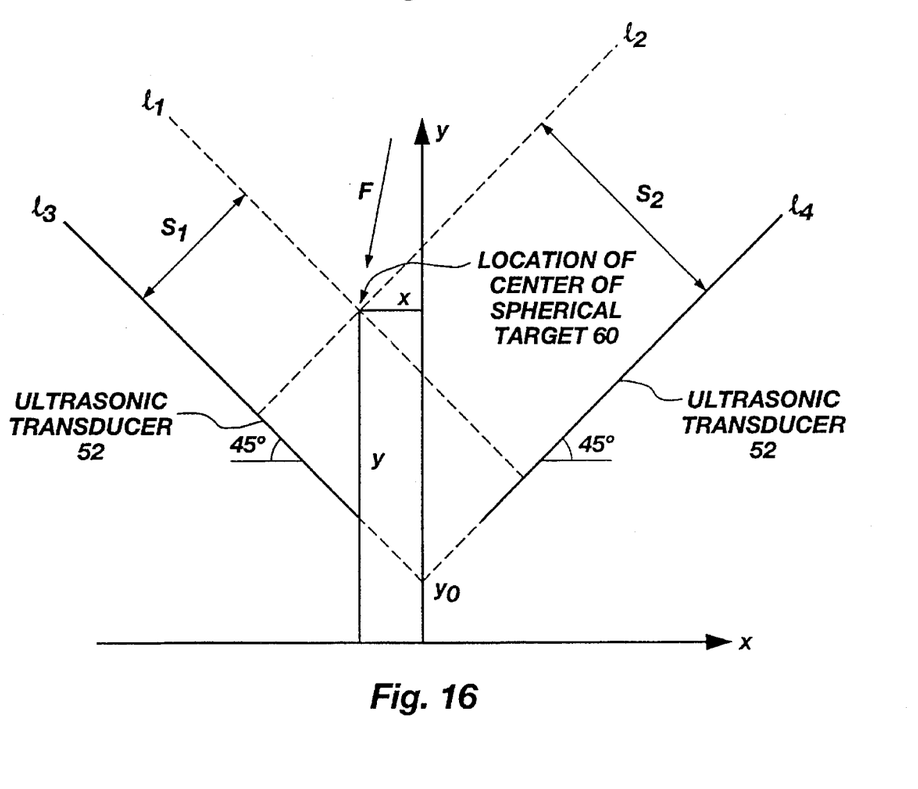
FIG. 16 is a simplified schematic of sensor geometry for mathematical purposes.

Following is a description of illustrative mathematics employed to determine the position (and therefore the forces) on a target 60 using the sensing geometry illustrated in FIGS. 1A and 1B, wherein one pair of transducers 52 is employed, the transducers being oriented at an exemplary angle Θ of 45° to the horizontal plane in which the transducers are located. For purposes of clarity, this geometry has been reproduced in much-simplified form in FIG. 16, with additional annotations as referred to below. The exact equations as set forth below would be straightforward to implement and would quickly run on a PC-class computer. FIG. 16 shows the sensing geometry for one pair of ultrasonic transducers 52. These transducers would measure normal force and one component of shear force in the plane of the transducers. The equations for the other shear force component (at right angles to the first) would be similar. The approach taken is that the time-off-light measurement (TOF) times the speed-of-sound÷2 plus the radius of the spherical target gives distances $S_1$ and $S_2$. Straight lines ($l_1$ and $l_2$) are drawn at these distances, parallel to the respective ultrasonic transducers ($l_3$ and $l_4$). These two lines ($l_1$ and $l_2$) intersect at a point (x, y) on the figure. This intersection point is the location of the diametrical center of the spherical or hemispherical target. The following should be noted:

1) The shear force is related to x, which is a function of $s_1-s_2$.
2) The normal force is related to y, which is a function of $s_1-s_2$.
3) The $$\frac{\sqrt{2}}{2}$$

factors are due to the transducers being oriented at 45°.
4) The actual forces are proportional to the change in TOF when no forces are applied vs when forces are applied (i.e., $t_{10}-t_1$ and $t_{20}-t_2$).
5) Adding the other two ultrasonic transducers does not affect the equations. It just adds two more equations of the same form.
6) Each pair of transducers gives a value for a shear force and the normal force. To improve accuracy, the two normal force values would be averaged.

Now:

For $l_2$: $y = mx + b$, $m = 1$ $y = x + b$ $b = y \ @ \ x = o$ $b = y_0 + \sqrt{2} \ s_2$ $\therefore y = x + y_0 + \sqrt{2} \ s_2$ For $l_4$: $y = mx + b$, $m = 1$ $y = x + b$ $y = b \ @ \ x = o$ $\therefore b = y_0$ $\therefore y = x + y_0$ For $l_3$: $y = mx + b$, $m = -1$ $y = -x + b$ $y = b \ @ \ x = o$ $\therefore b = y_0$ $\therefore y = -x + y_0$ For $l_1$: $y = mx + b$, $m = -1$ $y = -x + b$ $b = y_0 + \sqrt{2} \ s_1$ $\therefore y = -x + y_0 + \sqrt{2} \ s_1$ Intersection of $l_1$ and $l_2$:

$y = -x + y_0 + \sqrt{2} \ s_1$ $y = x + y_0 + \sqrt{2} \ s_2$ $x + y_0 + \sqrt{2} \ s_2 = -x + y_0 + \sqrt{2} \ s_1$ $2x = \sqrt{2} \ (s_1 - s_2)$ when $s_1 = s_2$, $x = o$ $\therefore x = \frac{\sqrt{2}}{2} (s_1 - s_2)$ $y = \frac{\sqrt{2}}{2} (s_1 - s_2) + y_0 + \sqrt{2} \ s_2$ $= y_0 + \frac{\sqrt{2}}{2} s_1 + \frac{\sqrt{2}}{2} s_2$ $\therefore y = y_0 \frac{\sqrt{2}}{2} (s_1 + s_2)$ $s_1 = (TOF)_1 \times \frac{c}{2}$ + radius of target -continued $s_2 = (TOF)_2 \times \frac{c}{2}$ + radius of target Where c=the speed-of-sound in the elastomer For forces, our calculations $\Delta x$ and $\Delta y$ $\therefore \Delta x = K_1 \{(t_{10}-t_1)-(t_{20}-t_2)\}$ =shear force $\Delta y = K_2 \{(t_{10}-t_1)+(t_{20}-t_2)\}$ =normal force Where $t_{10}$ is $(TOF)_1$, when no forces are applied, $t_{20}$ is $(TOF)_2$ when no forces are applied, $t_1$ and $t_2$ are $(TOF)_1$ and $(TOF)_2$ respectively, when a force F is applied and $K_1$ and $K_2$ are constants which include the speed-of-sound in the elastomer, rubber stiffness, and the factor $$\frac{\sqrt{2}}{2}.$$

Using four transducers spaced at 90° intervals about a spherical or hemispherical target, all transducers being angled at 45° to the target, the mathematical equations giving the shear force in terms of TOF are quite simple. First of all, the x, y, z coordinates of the center of the reflector are:

$$x = \frac{\sqrt{2}}{2} (t_1 - t_3) c_1, y = \frac{\sqrt{2}}{2} (t_2 - t_4) c_1 \text{ and}$$

$$z = z_0 + \frac{\sqrt{2}}{4} (t_1 + t_2 + t_3 + t_4) c$$

where $t_1$, $t_2$, $t_3$ and $t_4$ are the TOF's associated with pulses from each of the four transducers, and c is the speed-of-sound in the material disposed between the transducers and the target. Note, the above equations are only strictly true for a point target or reflector; for a real reflector target, a constant offset value has to be added. However, this offset cancels out of the equation when $\Delta x$ and $\Delta y$ are calculated. The forces corresponding to the change in position of the target are simply the change in coordinate value (from no force to force being applied to the sensor) times the appropriate rubber stiffness parameter (shear stiffness for $F_x$ and $F_y$, compressive stiffness for $F_z$, and constants such as $$\frac{\sqrt{2}}{2}$$

due to the geometry of the sensor). As is apparent from the equations immediately above, normal force $F_z$ can be obtained by averaging all four time-of-flight measurements from one sensor unit. The averaging process will increase the accuracy of the calculated value of $F_z$. Further, since differential time intervals are used in calculating the value of the two shear force components, the calculation can be made independent of temperature effects on the elastomer. The primary effect of temperature on the sensor is to cause the elastomer to expand and the speed-of-sound to decrease with an increase in temperature. Secondarily, elastomer stiffness also decreases somewhat with increasing temperature. If the above shear force equations am modified slightly by dividing the time difference by the sum of the two time intervals (e.g., $(t_1-t_3)/(t_1+t_3)$), then the effects of temperature on rubber thickness and speed-of-sound are eliminated.

While not set forth in detail, it will be readily understood that, through use of at least three basic sensor units 50 (either three- or four-transducer configuration) in a common plane and non-colinearly arranged, the three torque components $M_x$, $M_y$ and $M_z$ may be calculated from the difference in the force components at the three sensor unit sites.

While the present invention has been described in terms of the illustrated embodiments, those of ordinary skill in the art will readily understand and appreciate that it is not so limited. Many additions, deletions and modifications to the embodiments illustrated and described herein are possible without departing from the scope of the invention as hereinafter claimed.

What is claimed is:

1. A sensor for use in determining shear and normal components of a force applied thereto, comprising:
    a target for reflecting ultrasonic waves;
    at least two ultrasonic transducers aimed at said target, each of said transducers adapted to emit and detect ultrasonic signals, and each of said transducers being laterally and vertically offset from said target;
    a substantially acoustically-transparent, substantially acoustically-nonrefractive medium disposed between each of said transducers and said target; and
    compliant means supporting said target.

2. The sensor of claim 1, further including electronic driving circuitry for causing said transducers to emit ultrasonic signals and electronic timing circuitry for determining the transit time between the emission of a signal from a transducer and detection of the emitted signal after reflection from said target.

3. The sensor of claim 2, wherein said timing circuitry is also adapted to control the emission of said signals.

4. The sensor of claim 3, further including a microprocessor programmed to determine said shear and normal force components of said force from signal transit times, the speed-of-sound in said medium, and the degree of compliancy of said compliant means.

5. The sensor of claim 2, further including means for determining said shear and normal force components of said force in relation to transit times of said ultrasonic signals between said transducers and said target.

6. The sensor of claim 5, wherein said means for determining said shear and normal force components of said force is adapted to employ the speed-of-sound in said medium and the degree of compliancy of said compliant means in so determining.

7. The sensor of claim 1, wherein said at least two transducers are located in a common plane.

8. The sensor of claim 1, wherein said at least two transducers comprise four transducers located at 90° intervals around said target.

9. The sensor of claim 1, wherein said target presents a constant-radius, arcuate reflective surface to said transducers.

10. The sensor of claim 9, wherein said target comprises a hemisphere.

11. The sensor of claim 1, wherein said target is embedded in said compliant means.

12. The sensor of claim 1, wherein said compliant means comprises an elastomer, which also provides at least a segment of said medium.

13. The sensor of claim 12, wherein said elastomer is selected from a group comprising urethanes, silicone rubbers, neoprene rubbers, natural rubbers, plastics and gels.

14. The sensor of claim 1, wherein said transducers are selected from a group comprising PVDF films and ceramics.

15. A multi-sensor array for use in determining shear and normal components of a force applied thereto, comprising:
    a plurality of targets for reflecting ultrasonic waves, said targets being laterally separated and located at predetermined intervals;
    each of said targets having associated therewith at least two ultrasonic transducers adapted to emit and receive ultrasonic signals, said at least two transducers each being aimed at said target with which each of said transducers is associated and horizontally and vertically offset therefrom; and
    a substantially acoustically-transparent, substantially acoustically-nonrefractive medium disposed between each of said transducers and said targets; and
    compliant means supporting said targets.

16. The multi-sensor array of claim 15, wherein said targets are located at substantially equal intervals and in a common plane.

17. The multi-sensor array of claim 16, wherein said transducers are located in a common plane.

18. The multi-sensor array of claim 17, wherein said at least two transducers comprise four transducers located at 90° intervals around said targets.

19. The multi-sensor array of claim 15, wherein said at least two transducers comprise four transducers located at 90° intervals around said targets, two of said transducers being located in mutual opposition in a first common plane, and two of said transducers being located in mutual opposition in a second common plane.

20. The multi-sensor array of claim 15, wherein said targets each present a constant-radius, arcuate reflective surface to the transducers with which said target is associated.

21. The multi-sensor array of claim 20, wherein said targets comprise hemispheres.

22. The multi-sensor array of claim 15, wherein said targets are embedded in said compliant means.

23. The multi-sensor array of claim 15, wherein said compliant means comprises an elastomer, which also provides at least a segment of said medium.

24. The multi-sensor array of claim 23, wherein said elastomer is selected from a group comprising urethanes, silicone rubbers, neoprene rubbers, natural rubbers, plastics and gels.

25. The multi-sensor array of claim 15, wherein said transducers are selected from a group comprising PVDF films and ceramics.

26. The multi-sensor array of claim 15, further including electronic driving circuitry for causing said transducers to emit ultrasonic signals and electronic timing circuitry for determining the transit time between the emission of a signal from a transducer and detection of the emitted signal after reflection from the target at which said signal is aimed.

27. The multi-sensor array of claim 26, wherein said timing circuitry is also adapted to control the emission of said signals.

28. The multi-array sensor of claim 27, further including a microprocessor programmed to determine said shear and normal force such components of said force from signal transit times, the speed-of-sound in said medium, and the degree of compliancy of said compliant means.

29. A method of determining shear and normal force components of a force, comprising:
    arranging an acoustically-reflective target;
    providing at least two ultrasonic transducers horizontally and vertically offset from said target in a common plane, and aiming said transducers at said target from a common distance;
    compliantly supporting said target with a structure having known compliancy characteristics in a substantially acoustically-transparent, substantially acoustically-nonrefractive medium extending between each of said transducers and said target, said medium having known speed-of-sound;

applying said force to said target;

emitting an ultrasonic signal from each transducer toward said target, and timing the transit time between emission of each said signal and the emitted signal's return to the transducer from which the signal was emitted; and calculating shear and normal force components of said force from said transit times and said known speed-of-sound and compliancy characteristics.

30. The sensor array of claim 26, further including means for determining said shear and normal force components of said force in relation to transit times of said ultrasonic signals between said transducers and said targets.

31. The sensor array of claim 30, wherein said means for determining said shear and normal force components of said force is adapted to employ the speed-of-sound in said medium and the degree of compliancy of said compliant means in so determining.

* * * * *